US012754191B2

(12) United States Patent
Kauffmann

(10) Patent No.: US 12,754,191 B2
(45) Date of Patent: Oct. 6, 2026

(54) DRIED REAGENT POLYSACCHARIDE SURFACE AREA STABILIZATION

(71) Applicant: Siemens Healthcare Diagnostics Inc., Tarrytown, NY (US)

(72) Inventor: Aaron Kauffmann, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1135 days.

(21) Appl. No.: 17/435,439

(22) PCT Filed: Feb. 26, 2020

(86) PCT No.: PCT/US2020/019840

§ 371 (c)(1),
(2) Date: Sep. 1, 2021

(87) PCT Pub. No.: WO2020/180553

PCT Pub. Date: Sep. 10, 2020

(65) Prior Publication Data

US 2022/0163543 A1 May 26, 2022

Related U.S. Application Data

(60) Provisional application No. 62/813,297, filed on Mar. 4, 2019.

(51) Int. Cl.
*G01N 33/72* (2006.01)
*G01N 33/531* (2006.01)
*G01N 33/543* (2006.01)

(52) U.S. Cl.
CPC ......... *G01N 33/723* (2013.01); *G01N 33/531* (2013.01); *G01N 33/54366* (2013.01)

(58) Field of Classification Search
CPC ........... G01N 33/723; G01N 33/54366; G01N 33/54393
USPC .......................................................... 436/501
See application file for complete search history.

(56) References Cited

U.S. PATENT DOCUMENTS

| | | | |
|---|---|---|---|
| 7,285,426 B2 | 10/2007 | Bohannon et al. | |
| 7,919,294 B2 | 4/2011 | Franco De Sarabia Rosado et al. | |
| 8,603,828 B2 | 12/2013 | Walker et al. | |
| 2004/0189311 A1* | 9/2004 | Glezer | B01J 19/0046 324/444 |
| 2006/0264779 A1 | 11/2006 | Kemp et al. | |

FOREIGN PATENT DOCUMENTS

| | | | |
|---|---|---|---|
| EP | 2760998 A1 | 8/2014 | |
| EP | 3153858 A1 | 4/2017 | |
| EP | 2063866 B2 | 8/2017 | |
| WO | WO-2018017332 A1 * | 1/2018 | B01L 3/502 |
| WO | WO-2018069056 A1 * | 4/2018 | B01L 3/502707 |

OTHER PUBLICATIONS

Moradi et al., Review on current state, challenges, and potential solutions in solid-state batteries research, Journal of Energy Storage 73 (2023) 109048, p. 4, right col. third paragraph. (Year: 2023).*
Allaby, Michael, editor, "Tensile Strength", Illustrated Dictionary of Science, Andromeda, 1st ed., Windmill Books (Andromeda International), 1988, Credo Reference, accessed on Sep. 19, 2025 at 10:30 am. (Year: 1988).*
Hoehne et al., Adsorption of Monoclonal Antibodies to Glass Microparticles, Journal of Pharmaceutical Sciences, vol. 100, No. 1, Jan. 2011. (Year: 2011).*
International Search Report and Written Opinion of International Application No. PCT/US2020/019840 dated Jun. 23, 2020.
Ohtake et al., "Interactions of formulation excipients with proteins in solution and in the dried state", 2011, Advanced Drug Delivery Reviews, pp. 1-5.
Remmele, Jr. et al., "Development of Stable Lyophilized Protein Drug Products", Current Pharaceutical Biotechology, vol. 13, No. 3, Mar. 1, 2012, pp. 471-496.

* cited by examiner

*Primary Examiner* — Gregory S Emch
*Assistant Examiner* — Omar Ramadan

(57) ABSTRACT

Non-limiting embodiments of a modified solid reagent zone comprising at least hydrophilic polysaccharide and/or at least one hydrophilic non-polysaccharide polymer for use in the conductance of at least one diagnostic assay, as well as kits and methods of use and production related thereto.

16 Claims, 11 Drawing Sheets

DRIED REAGENT POLYSACCHARIDE SURFACE AREA STABILIZATION

CROSS REFERENCE TO RELATED APPLICATIONS

The present patent application claims the benefit of provisional patent application Ser. no. 62/813,297, filed on Mar. 4, 2019, the entire contents of which are hereby incorporated herein by reference.

STATEMENT REGARDING FEDERALLY FUNDED RESEARCH OR DEVELOPMENT

Not Applicable.

TECHNICAL FIELD

The presently disclosed and claimed inventive concept(s) relate to a device(s), kit(s), and method(s) that increase the stability and/or shelf life of component(s) and/or reagent(s) utilized for the conductance of at least one diagnostic assay. More specifically, the presently disclosed and claimed inventive concept(s) relate to non-limiting embodiments of a modified reaction cassette and/or housing that comprises and/or consists of an improved antibody reaction zone for use in the conductance of at least one diagnostic assay, as well as kits and methods of use related thereto.

BACKGROUND

Numerous devices and methods exist for detecting analytes that may be present in a fluid sample. Such devices have been proven to be effective in diagnostic assays that detect the presence and quantity of certain analytes indicative of a patient's health, including, but not limited to, glycated hemoglobin (HbA1c), microalbumin and creatinine, and lipid-based analytes, such as cholesterol, triglycerides, and/or high-density lipoproteins. However, the results obtained from the conductance of such analyte detection assay(s) may be inaccurate and/or biased due to, for instance, phenotypic changes in reaction zones that comprise and/or consist of at least one diagnostic assay reagent (such as, by way of example only, an analyte-detection antibody utilized and/or contained within a reaction vessel for the conductance of at least analyte detection assay). When phenotypic changes occur to the reaction zones, for instance, due to storage of the reaction vessel over a period of time prior to use, the accuracy and efficacy of the reaction zones are decreased. These structural deficiencies in the reaction zones may result, by way of example, in the incomplete capture of an analyte of interest that is present in a patient's liquid test sample, thereby resulting in bias in the reported concentration(s) of such analyte(s) of interest. In addition, the repeated bias of individual diagnostic assays/tests resulting from the use of structurally deficient reaction zones increases the coefficient of variation (% CV) obtained from the collective dataset, thereby decreasing the accuracy and repeatability of the diagnostic assay(s).

Accordingly, there is a need for improved devices and methods that decrease, mitigate, or eliminate phenotypic variations in a reaction zone for use in at least one diagnostic assay. Such decrease, mitigation, or elimination thereby extends the shelf-life and usability period for a reaction vessel(s) that comprises the reaction zone(s) and thereby decrease inaccuracies in diagnostic assay results associated with and/or introduced by such variations. It is to such devices and methods, as well as kits related thereto, that the presently disclosed and claimed inventive concept(s) is directed.

DETAILED DESCRIPTION

Figure 1:
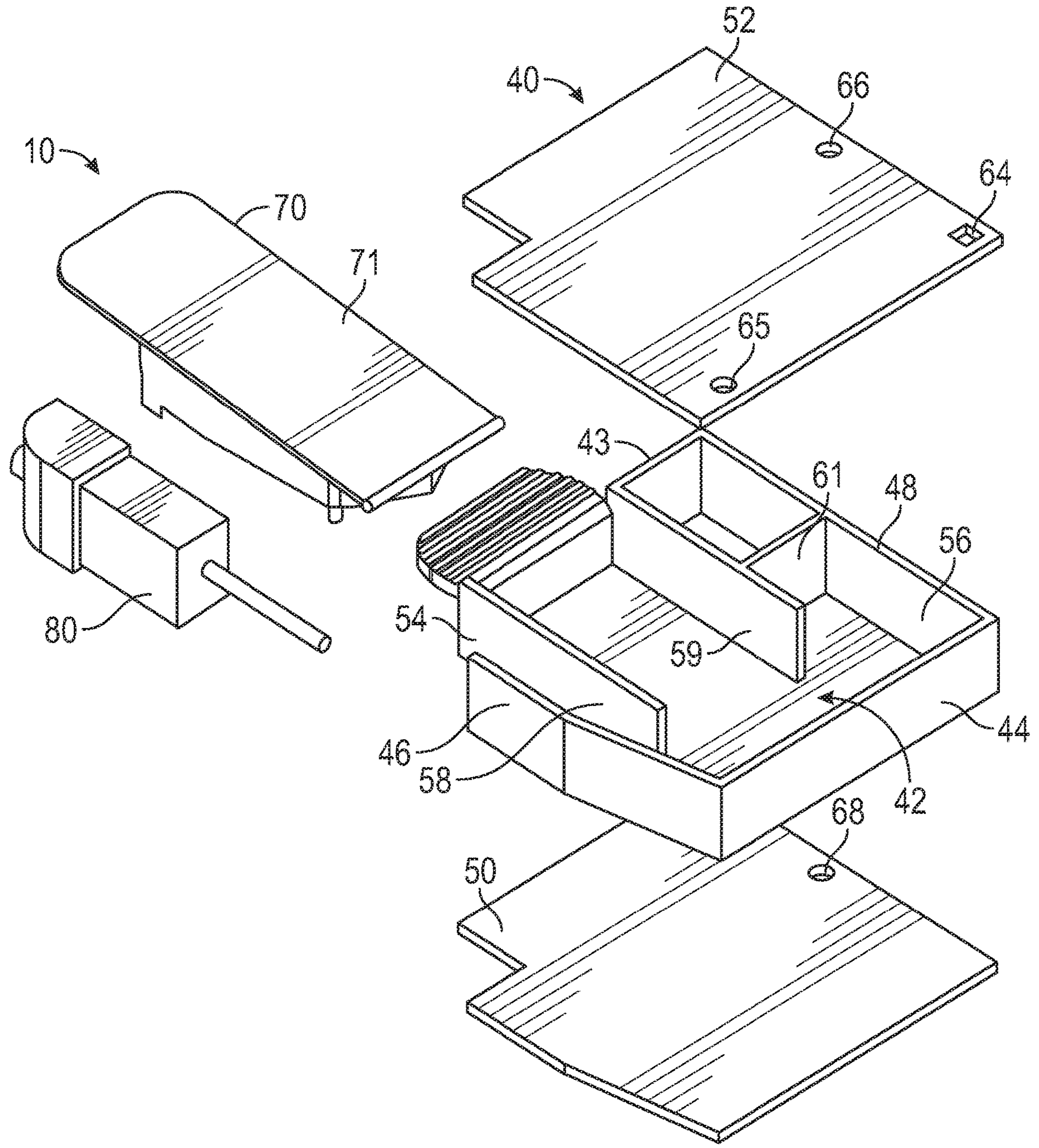
FIG. 1 is a top view of one embodiment of the analytical reaction kit constructed in accordance with the presently disclosed and/or claimed inventive concept(s).

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the devices, kits, and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or 0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "liquid test sample" as used herein will be understood to include any type of biological fluid sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), intestinal fluid, intraperotineal fluid, cystic fluid, sweat, interstitial fluid, tears, mucus, urine, bladder wash, semen, combinations, and the like. As used herein, the term "volume" as it relates to the liquid test sample utilized in accordance with the presently disclosed and claimed inventive concept(s) means from about 0.1 microliter to about 100 microliters, or from about 1 microliter to about 75 microliters, or from about 2 microliters to about 60 microliters, or less than or equal to about 50 microliters.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

Turning now to particular embodiments, the presently disclosed and claimed inventive concept(s) relate to a device(s), kit(s), and method(s) for dispensing at least two liquid reagents for use in analyte(s) detection assays. More specifically, the presently disclosed and claimed inventive concept(s) relate to a modified apparatus present within a reaction cassette and/or housing that is capable of dispensing at least two liquid reagents for use in analyte(s) detection assays, as well as kits and methods of use related thereto.

It is contemplated that virtually any reagent used in the fields of biological, chemical, or biochemical analyses and assays could be used in the devices, kits, and methods of the presently claimed and disclosed inventive concept(s). It is contemplated that these reagents may undergo physical and/or chemical changes when bound to an analyte of interest whereby the intensity, nature, frequency, or type of signal generated by the reagent-analyte complex is directly proportional or inversely proportional to the concentration of the analyte existing within the fluid sample. These reagents may contain indicator dyes, metal, enzymes, polymers, antibodies, and electrochemically reactive ingredients and/or chemicals that, when reacting with an analyte(s) of interest, may exhibit change in color.

Any method of detecting and measuring the analyte in a fluid sample can be used in the devices, kits, and methods of the presently claimed and inventive concepts. A variety of assays for detecting analytes are well known in the art and include, but are not limited to, chemical assays, enzyme inhibition assays, antibody stains, latex agglutination, latex agglutination inhibition and immunoassays, such as, radioimmunoassays. The term "antibody" herein is used in the broadest sense and refers to, for example, intact monoclonal antibodies, polyclonal antibodies, multi-specific antibodies (e.g., bispecific antibodies), and to antibody fragments that exhibit the desired biological activity (e.g., antigen/analyte-binding). The antibody can be of any type or class (e.g., IgG, IgE, IgM, IgD, and IgA) or sub-class (e.g., IgG1, IgG2, IgG3, IgG4, IgA1, and IgA2).

While immunoassays (including, but not limited to, sequential analytical chemical and immunoassays) are primarily discussed herein for the detection of at least one analyte of interest present in a liquid test sample, a person having ordinary skill in the art should readily understand that the presently disclosed and claimed inventive concept(s) are not strictly limited to immunoassays and may include, by way of example and not by limitation, chemical and chemical-based assays, nucleic acid assays, lipid-based assays, and serology-based assays. Immunoassays, including radioimmunoassays and enzyme-linked immunoassays, are useful methods for use with the presently claimed and disclosed inventive concepts. A variety of immunoassay formats, including, for example, competitive and non-competitive immunoassay formats, antigen/analyte capture assays and two-antibody sandwich assays can be used in the methods of the invention. Enzyme-linked immunosorbent assays (ELISAs) can be used in the presently claimed and disclosed inventive concepts, as well. In the case of an enzyme immunoassay, an enzyme is typically conjugated to a second antibody, generally by means of glutaraldehyde, periodate, hetero-bifunctional crosslinking agents, or biotin-streptavidin complexes. As will be readily recognized, however, a wide variety of different conjugation techniques exist which are readily available for use with the presently disclosed and claimed inventive concept(s) to one skilled in the art.

Assays, including, but not limited to, immunoassays, nucleic acid capture assays, lipid-based assays, and serology-based assays, can be developed for a multiplexed panel of proteins, peptides, and nucleic acids which may be contained within a liquid test sample, with such proteins and peptides including, for example but not by way of limitation, albumin, microalbumin, cholesterol, triglycerides, high-density lipoproteins, low-density lipoproteins, hemoglobin, myoglobin, $\alpha$-1-microglobin, immunoglobins, enzymes, proteins, glycoproteins, protease inhibitors, drugs, cytokines, creatinine, and glucose. The device(s), kit(s), and method(s) disclosed and/or claimed herein may be used for the analysis of any fluid sample, including, without limitation, whole blood, plasma, serum, or urine.

Referring now to FIG. 1, shown therein is a non-limiting embodiment of a detailed, exploded view of an analytical research kit 10 constructed in accordance with the presently disclosed and/or claimed inventive concept(s). The analytical research kit 10 comprises a reaction cassette/housing 40, a liquid reagent container 70, and a capillary 80, which may be utilized both for obtaining a liquid test sample from a patient and introducing such sample into the reaction cassette 40.

The reaction cassette/housing 40 comprises a body 42 formed by the top perimeter side 43, a bottom perimeter side 44, a first perimeter side 46, a second perimeter side 48, and a bottom portion 50. The reaction cassette 40 further comprises a top portion 52 that is used to seal the body 42 of the reaction cassette 40 after the liquid reagent container 70 containing at least one diagnostic assay buffer(s) and/or liquid assay reagent(s) has been incorporated into the reaction cassette 40 as described and/or claimed herein. Such seal can be accomplished via any method commonly known in the art, including, without limitation, adhesive(s), glue, sonic welding, laser welding, and/or any permanent fastener (s).

In one embodiment, the body 42 of the reaction cassette 40 is constructed such that the body is formed via the connection of the top perimeter side 43, the bottom perimeter side 44, the first perimeter side 46, and the second perimeter side 48 to the bottom portion 50. Such connection can be via any method commonly known in the art, including, without limitation, adhesive(s), glue, sonic welding, laser welding, and/or any permanent fastener(s). In another embodiment, the body 42 can be constructed such that the top perimeter side 43, the bottom perimeter side 44, the first perimeter side 46, the second perimeter side 48, and the bottom portion 50 is one contiguous piece, for instance, by way of example only, one contiguous piece of plastic.

The reaction cassette 40 has a substantially horizontal axis of rotation. While the external dimensions of the reaction cassette 40 are not critical, in one non-limiting embodiment of the presently disclosed and/or claimed inventive concept(s), the reaction cassette 40 has a height and width of about 3 centimeters to about 15 centimeters and a thickness of about 0.25 centimeters to about 2 centimeters. In one embodiment, the dimensions of the reaction cassette 40 comprise a height and width of about 6 centimeters and a thickness of about 1 centimeter.

In one non-limiting embodiment, the body 42 of the reaction cassette 40 further comprises a first inner wall 58 and a second inner wall 59, wherein the first inner wall 58 and the second inner wall 59 extend downward from the top perimeter wall 43 and are positioned opposite of one another and substantially perpendicular to the top perimeter wall 43 and the bottom perimeter wall 44. The first perimeter side 46, together with the second perimeter side 48, the bottom portion 50, and the top portion 52 form a reaction chamber 56, a portion of which is U-shaped and formed by a third inner wall 61 which extends between and substantially perpendicular to the second inner wall 59 and the second perimeter side 48. The reaction chamber 56 is in fluid communication with the inlet 54, thereby allowing a liquid test sample (not shown) to be introduced via the capillary 80 into the reaction chamber 56 of the reaction cassette 40. Once the body 42 of the reaction cassette 40 has been sealed by the top portion 52 following the incorporation of the liquid reagent container 70 into the reaction cassette 40, an inlet 54 is thereby formed between the first perimeter side 46 and the first side wall 58, the inlet 54 being substantially parallel to the first perimeter side 46 and the first side wall 58 and extending from the top perimeter side 43 downward toward the bottom perimeter side 44 of the reaction cassette 40. The inlet 54 is capable of securely receiving the capillary 80 such that the liquid test sample (not shown) is introduced from the capillary 80 into the reaction chamber 56 of the reaction cassette 40. While a capillary 80 is shown in the Figures as introducing the liquid test sample (not shown) into the reaction chamber 56 of the reaction cassette 40, it should be readily understood to a person having ordinary skill in the art that the liquid test sample (not shown) can be introduced into the reaction cassette 40 via any device capable of introducing a liquid a test sample, including, by way of example and not by way of limitation, a pipette(s). In addition, the inlet 54 can be stoppered, plugged, or otherwise closed subsequent to the introduction of the liquid test sample into the reaction cassette 40 so as to prevent liquid loss during the course of the methodologies described herein, including, but not limited to, assays, including immunoassays.

With specific reference to the liquid reagent container 70, while the figures depict embodiments of the liquid reagent container 70 as comprising a single cavity 75 (shown in FIG. 2), it should be readily understood to a person having ordinary skill in the art that the liquid reagent container 70 may be comprised of any number of cavities. By way of example and not by way of limitation, the liquid reagent container 70 may comprise 1, 2, 3, 4, 5, 6, 7, 8, 9, 10, 15, 20, 25, 50 or any number of cavities capable of being manufactured for incorporation in liquid reagent container 70. As shown in FIG. 1, the liquid reagent container 70 comprises a flexible cover 71. The flexible cover 71 is removably affixed to the liquid reagent container 70 to seal the container and the at least one cavity 75, thereby sealing in and preventing the discharge of the at least one liquid reagent from the at least one cavity 75 of the container 70. When the liquid reagent container 70 is oriented in a substantially vertical position (as shown in greater detail in FIG. 2) within the reaction cassette 40, the flexible cover 71 can be removed by a user to allow for the gravitational dispensing of the at least one liquid reagent/buffer from the at least one cavity 75. In one non-limiting embodiment, the liquid reagent container 70 is fabricated as a molded component formed of a rigid plastic material (so as to avoid deformation of the container 70 upon removal of the flexible cover 71 therefrom by a user), including, for example, high-density polyethylene; however, the container 70 may be constructed of any material capable of accomplishing the presently disclosed and/or claimed inventive concept(s). The flexible cover 71 may be, by way of example only, constructed of a vapor and liquid impermeable material, including, for example, a plastic laminate material or aluminum foil material. In one embodiment, the flexible cover 71 is affixed to the container 70 by a heat-activated peelable adhesive that leaves substantially no residue on the container 70 when the flexible cover 71 is removed by a user. In one embodiment, the flexible cover 70 may be constructed and configured to comprise a pull tab portion, which can be grasped and pulled by a user to remove the flexible cover 71 from the reaction cassette 70.

Figure 2:
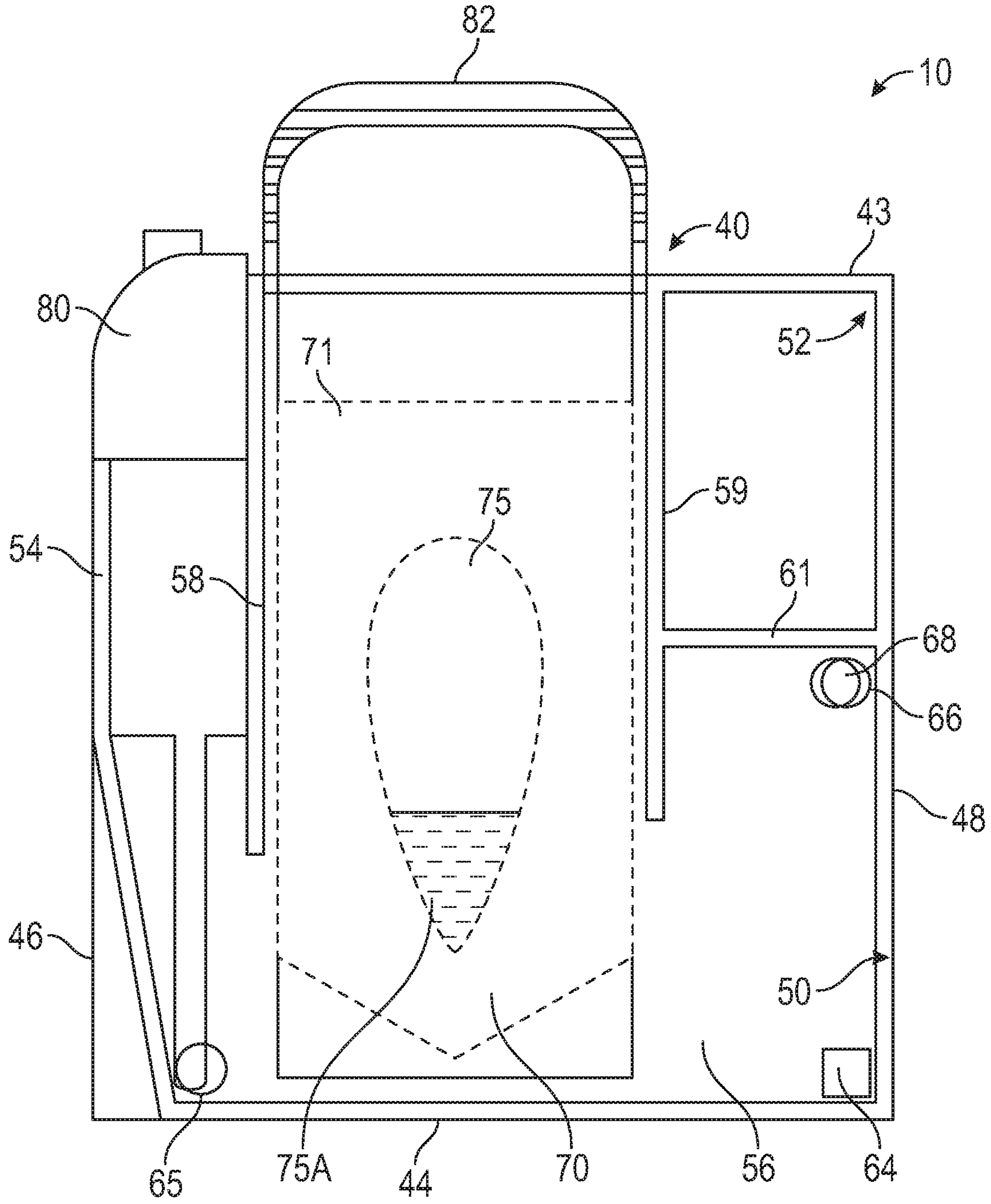
FIG. 2 are top views of one embodiment of the analytical reaction kit being used for the detection of at least one analyte present in a liquid test sample in accordance with the methodologies disclosed and/or claimed herein.

Referring now to FIG. 2, shown therein is one non-limiting embodiment of the analytical reaction kit 10 which comprises a liquid reagent container 70 which has been incorporated into a reaction cassette 40 and the capillary 80 which has been securely received into the inlet 54 of the reaction cassette 40. As shown in the FIG. 2, the liquid reagent container 70 remains closed and sealed by the flexible cover 71 thereby sealing in the liquid reagent/buffer 75A within the cavity 75. In one non-limiting embodiment, the liquid reagent container 70 is affixed within the reaction cassette 40 whereby the container 70 is positioned so as to secure between the first inner wall 58 and the second inner wall 59.

In one embodiment and as shown in FIG. 2, positioned along the reaction chamber 56 is a sample read window 64, a first solid reagent zone 65, a second solid reagent zone 66, and a third solid reagent zone 68. While shown in the Figures as comprising three individual solid reagent zones, it should be understood to a person having ordinary skill in the art, that any number of solid reagent zones may be used (or may be totally absent from reaction cassette 40) and positioned at any location(s) along the reaction chamber 56 in order to accomplish the presently disclosed and/or claimed inventive concept(s). The sample read window 64 can be, by way of example only and not by way of limitation, a transparent cuvette window or an optical window which permits the accurate measurement of detectable signals in the area of the sample read window 64. In one embodiment, the first solid reagent zone 65 is substantially located at a corner of the reaction cassette 40 formed from the perpendicular intersection of the first perimeter wall 46 and the bottom perimeter wall 44 wherein the first solid reagent zone 65 is formed on the top portion 52 of the reaction cassette 40. In one embodiment, the second solid reagent zone 66 and the third solid reagent zone 68 are substantially located at a corner of the reaction cassette 40 formed from the perpendicular intersection of the second perimeter wall 48 and the third inner wall 61 wherein the second solid reagent zone 66 is formed on the top portion 52 of the reaction cassette 40 and the third solid reagent zone 68 is formed on the bottom portion 50 of the reaction cassette 40. When present, the solid reagent zones 65, 66, and 68 are incorporated with solid analytical reagents for performing a particular analytical assay procedure. The solid analytical reagents are, in one embodiment, present in the solid reagent zones in a substantially dry (for instance, by way of example only, substantially dried via convection and/or conduction drying procedure(s)), water soluble, suspendable or dissolvable form, and can be incorporated along the reaction chamber 56 according to methods known in the art, such as, for example, by noncovalent binding techniques, absorptive techniques, and the like, in the desired order in which they are to be sequentially contacted with a liquid test sample. In one embodiment, the solid reagent zones 65, 66, and 68, when present, are defined in the form of substantially flat, raised portions or mesa-shaped nodes on the surface of the selected area of the reaction chamber 56, in which the raised upper surface of each node is from about 0.005 inches to about 0.02 inches elevated above or below a surface of the reaction chamber 56.

In one non-limiting embodiment of the presently disclosed and/or claimed inventive concept(s), the first solid reaction zone 65 comprises an oxidant (such as, for example, ferricyanide) which, as described in further detail hereinbelow, may be formulated, manufactured, and/or combined with at least one dye, the at least one dye having a known extinction coefficient when interrogated by particular wavelength(s) of light.

The second solid reaction zone 66 and the third solid reaction zone 68 comprise an agglutinator and an antibody-latex (for instance, by way of example only, a glycated hemoglobin A1c antibody), respectively. However, it should be readily understood to a person having ordinary skill in the art, that any compound, composition, and/or molecule can be used on the solid reagent zones in order to accomplish the presently disclosed and/or claimed inventive concept(s), including, without limitation, detection of at least one analyte(s) of interest present in a liquid test sample. In addition, it should be understood to a person having ordinary skill in the art that the presently disclosed and/or claimed inventive concept(s) can be accomplished in the absence of any or all of the first solid reagent zone 65, the second solid reagent zone 66, and the third solid reagent zone 68. In such an instance, the at least one liquid reagent/buffer 75A is capable of detecting at least one analyte(s) present in a liquid test sample in the absence of one or all of the solid reagent zones 65, 66, and/or 68.

With respect to the third solid reagent zone 68, and as discussed in greater detail hereinbelow, in one non-limiting embodiment, the third solid reagent zone 68 comprises and/or consists of one or more highly-concentrated sugars combined with at least one hydrophilic polysaccharide.

Figure 3A:
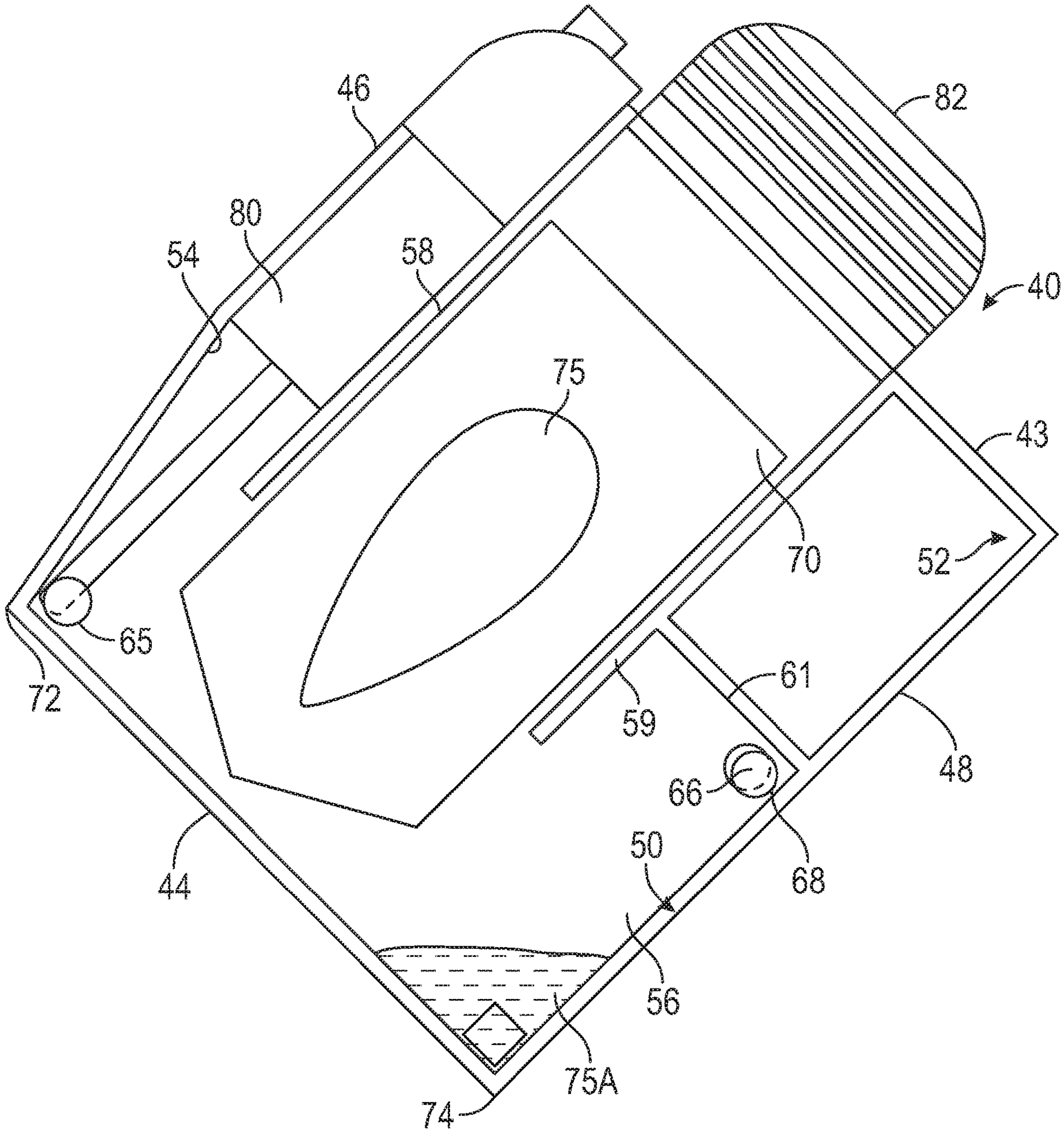
FIGS. 3A-3D are top views of another embodiment of the analytical reaction kit being used for the detection of at least one analyte present in a liquid test sample in accordance with the methodologies disclosed and/or claimed herein.
Figure 3B:
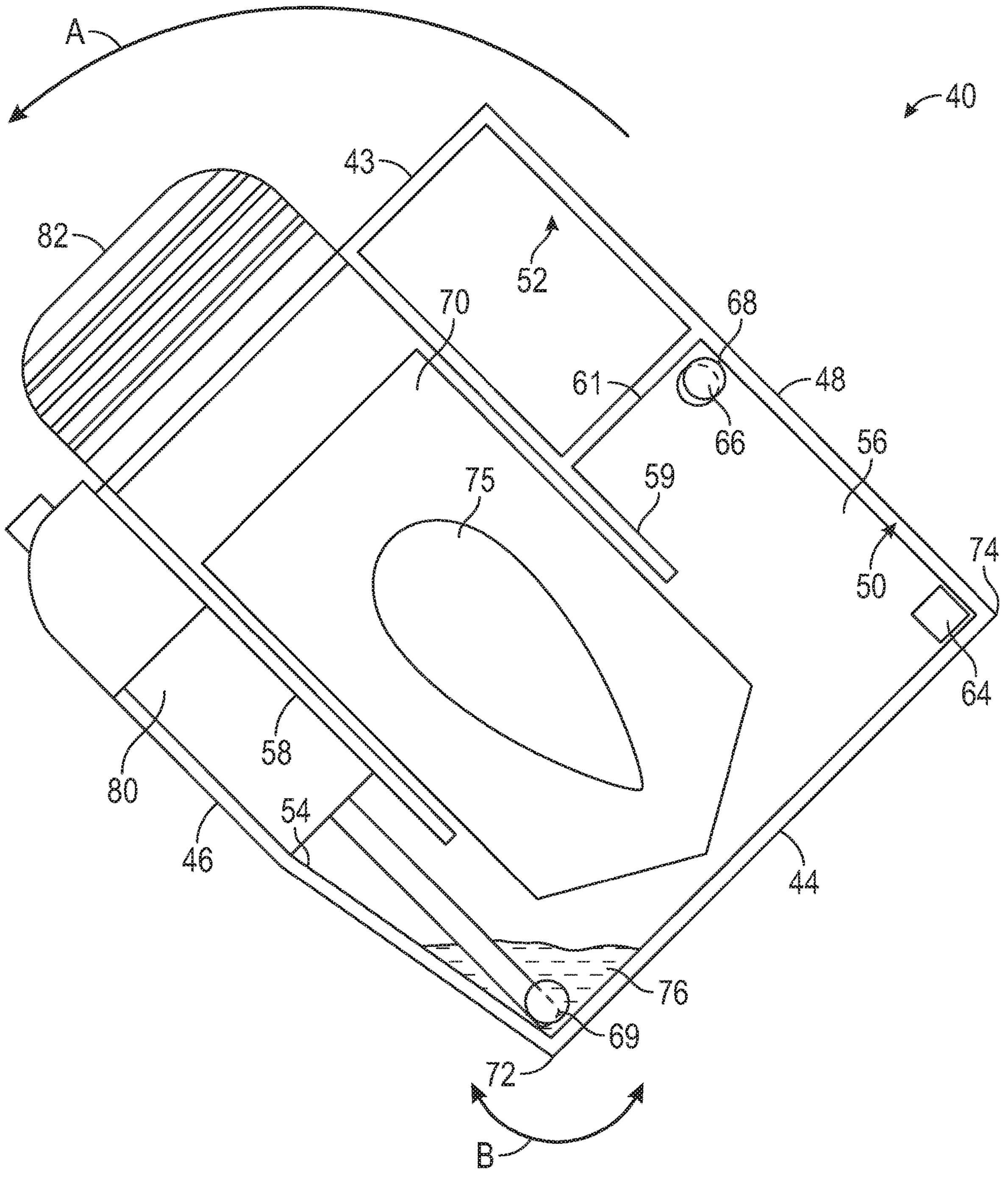
Figure 3C:
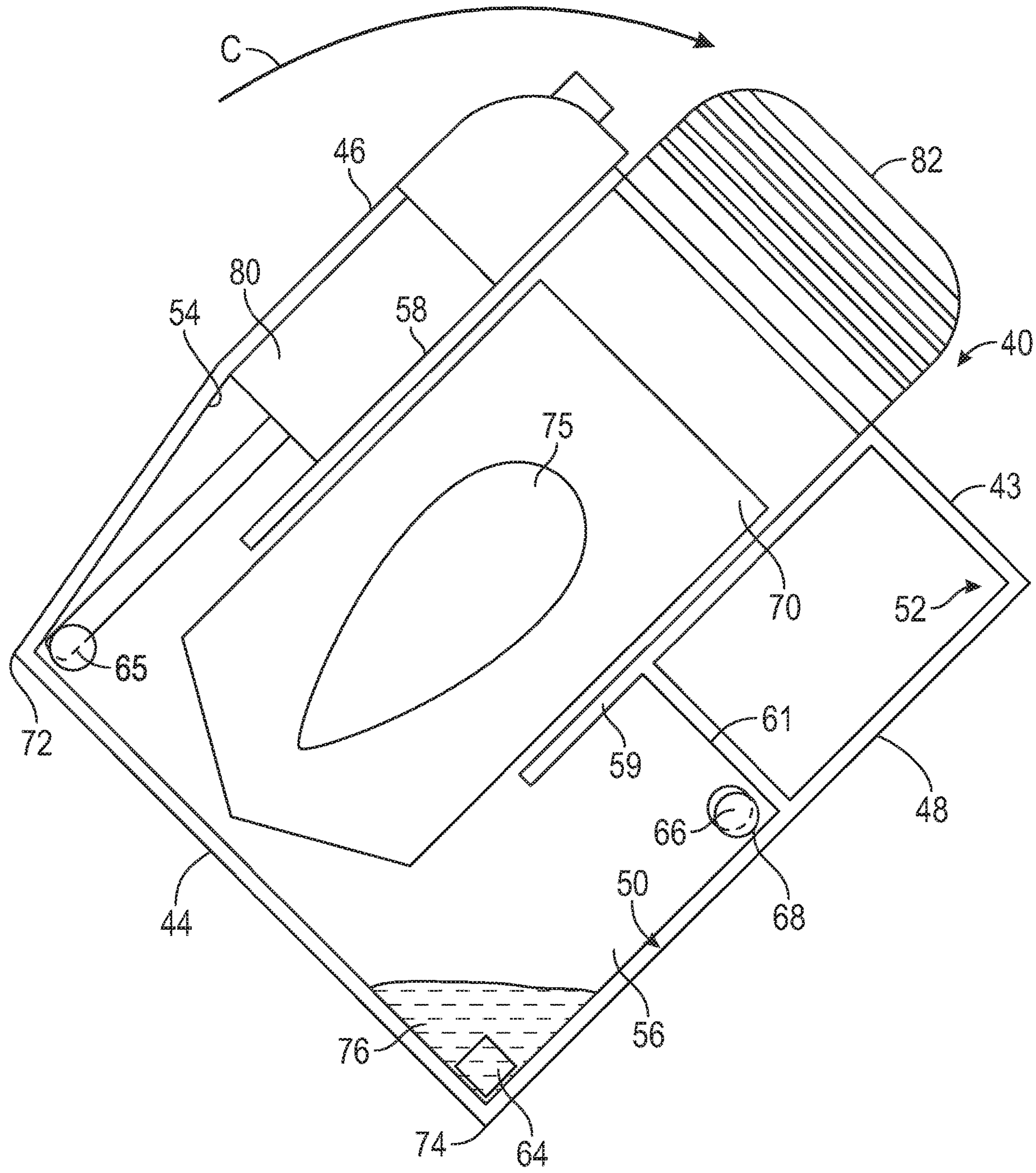

Referring now to FIGS. 3A-3D, shown therein is one embodiment of an analytical reaction cassette 40 constructed in accordance with the presently disclosed and/or claimed inventive concept(s) being used in a method of the presently disclosed and/or claimed inventive concept(s) to detect at least one analyte(s) of interest present in a liquid test sample. While FIGS. 3A-3C show a first solid reagent zone 65, a second solid reagent zone 66, and a third solid reagent zone 68, as described above, and the liquid reagent/buffer 75A, a person having reasonable skill in the art should readily understand that the presently disclosed and/or claimed methodology(-ies) may be accomplished via a combination of any number of solid reagents (present on solid reagent zones) and liquid reagents. The reaction cassette 40 is shown in various rotational positions to further illustrate the gravitational flow and mixing of the liquid test sample (not shown), the liquid reagent/buffer 75A and the first solid reagent zone 65, the second solid reagent zone 66, and the third solid reagent zone 68 along the reaction chamber 56 as the reaction cassette 40 is rotated about a substantially horizontal axis. The solid arrows shown outside of the reaction cassette 40 indicate the direction of rotation of the reaction cassette 40 about the horizontal axis.

It is to be understood that FIGS. 3A-3D are for purposes of illustration only and are not intended to limit the number, nature, or manner of incorporation of analytical reagents (solid and/or liquid) into the reaction cassette 40, or the sequence or direction of rotation of the reaction cassette 40. For example, and as described hereinabove, although three solid assay reagent zones 65, 66, and 68 and the at least one liquid reagent/buffer cavity 75 of the liquid reagent container 70 are shown, other assay procedures, including, but not limited to immunoassays procedures, and, more specifically, immunoturbidimetric assay procedures, can also be performed in the reaction cassette 40 in which the number of analytical reagents (solid and/or liquid) may vary depending on the particular assay requirements. In addition, the reaction cassette 40 may include less than the required number of analytical reagents (solid and/or liquid) for performing an analytical assay procedure where one or more reaction mixtures thereof can first be performed outside of the reaction cassette 40 and then introduced into the reaction cassette 40 to complete the assay.

An illustrative, non-limiting method of using the reaction cassette 40 depicted in FIGS. 1 and 2 will now be described as shown in and with reference to FIGS. 3A-3D. As shown in these Figures, the flexible cover 71 has been removed, thereby allowing the gravitational dispensing and flow of the liquid reagent/buffer 75A from the at least one liquid reagent/buffer cavity 75 into the reaction chamber 56. However, it should be understood to a person having ordinary skill in the art that the flexible cover 71 is present upon insertion of the reaction cassette 40 into the suitable instrument, apparatus, or system and is selectively removed at the appropriate time (as described below) by a user during the conductance of the at least one assay test. As discussed herein, the various rotation and oscillation movements of the reaction cassette 40 can be performed manually, but in most cases will be performed by a suitable instrument, apparatus, or system, including, without limitation, the DCA Vantage® Analyzer commercially available from Siemens Healthcare Diagnostics, Inc.

In one embodiment, the first step is to provide the reaction cassette 40 into a holder mechanism of a diagnostic instrument, apparatus, or system such that a second corner 74 of the reaction cassette 40, which is formed by the substantial perpendicular intersection of the second perimeter side 48 and the bottom perimeter side 44, is positioned in a downward orientation. Following insertion of the reaction cassette 40 into the suitable instrument, apparatus, or system, a liquid test sample (not shown) is drawn into the capillary 80 and the capillary 80 containing the liquid test sample is inserted into inlet 54 whereby the liquid test sample contained in the capillary 80 is proximally located near a first corner 72 of the reaction cassette 40. Upon insertion of the capillary 80 into the inlet 54 of the reaction cassette 40, the capillary 80 seals the inlet 54 of the reaction cassette 40. The portion of the capillary 80 near the first corner 72 is configured such that when the capillary 80 is positioned as described above, the portion of the capillary 80 containing the liquid test sample is capable of being contacted by a liquid in the reaction chamber 56, such as the liquid reagent/buffer 75A introduced into the reaction chamber 56 from the at least one cavity 75 of the liquid reagent container 70.

As shown in FIG. 3A, the liquid reagent/buffer 75A contained within the at least one cavity 75 is introduced into the reaction chamber 56 by pulling the pull tab portion of the flexible cover 71 in a direction away from the reaction cassette 40. The liquid reagent/buffer 75A (which, for example, may be a non-reactive buffer solution) is freely dispensed and flows by gravity into the second corner 74 of the reaction chamber 56. A blank absorbance reading can be taken through the sample read window 64, for instance, via a spectrophotometer, as the starting position and baseline absorbance with the second corner 74 oriented downward.

As shown in FIG. 3B, the reaction cassette 40 may then be rotated in a counter-clockwise direction (as shown by solid directional arrow A) and oscillated (as shown by solid arrow B) whereby the liquid reagent/buffer 75A is transported by gravity along the reaction chamber 56 from the second corner 74 and brought into contact with the first corner 72 and the portion of the capillary 80 containing the liquid test sample (not shown). It is to be understood that, in accordance with the presently disclosed and/or claimed inventive concept(s), the turbulence caused by the liquid reagent/buffer 75A impacting the first corner 72 during oscillation of the reaction cassette 40 results in the removal of the liquid test sample from the capillary 80 to form a first reaction mixture 76. In addition, in the presence of the first solid reagent zone 65, the oscillation allows for the solubilization of the at least one solid analytical reagent present on the first solid reagent zone 65 by the liquid reagent/buffer 75A. The reaction cassette 40 can be maintained in a stationary position for a predetermined amount of time to allow the at least one analyte(s) present in the first reaction mixture 76 to sufficiently interact and/or associate with the first liquid reagent/buffer 75A and/or the solid analytical reagent (such as, by way of example, an oxidant such as ferricyanide).

Where the first reaction mixture 76 provides one or more detectable responses or measureable characteristics (for instance, by way of example only, a first absorbance and a second absorbance) which is required or desired to be measured according to a particular assay protocol, as shown in FIG. 3C, the reaction cassette 40 is rotated in a clockwise direction (as shown by the solid directional arrow C) such that the first reaction mixture 76 is transported by gravity to the sample read window 64 in the second corner 72, and the reaction cassette 40 is maintained in a stationary position. Any such detectable response provided by the first reaction mixture 76 can then be measured, and the remaining assay steps, if necessary, can be carried out subsequent thereto. By way of example only and not by way of limitation, the detectable responses may be a total hemoglobin measurement where the liquid test sample is whole blood, for example, such as when performing an assay for the percent of glycated hemoglobin (HbA1c) in a whole blood sample, as well as a measurement of the total volume of the liquid reagent/buffer 75A present in the first reaction mixture 76.

Figure 3D:
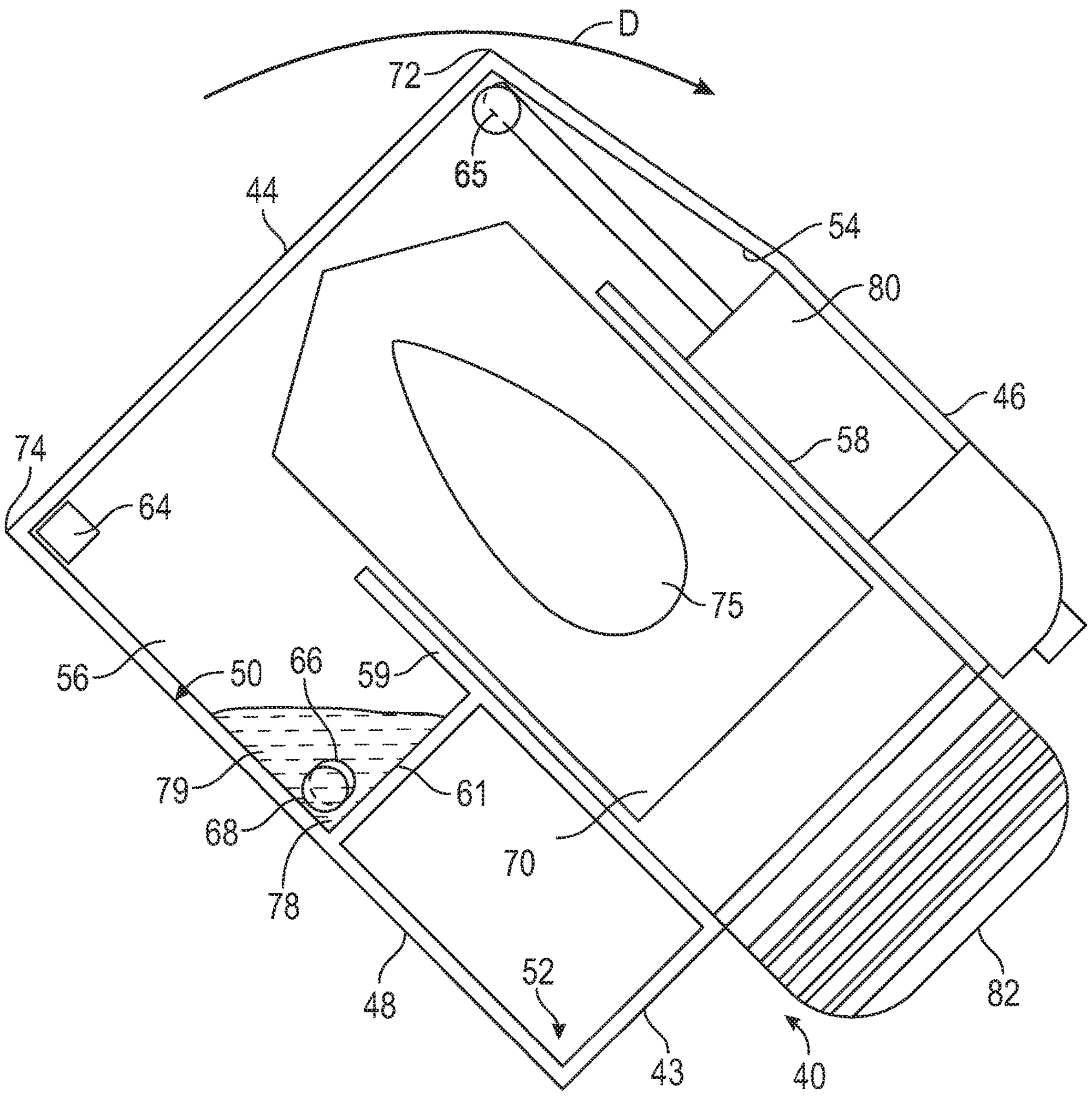

As depicted in FIG. 3D, once the first detectable response is detected and measured in the second corner 72, the analytical research kit 40 may then be rotated in a clockwise direction (as shown by solid directional arrow D) such that the first reaction mixture 76 is transported via gravity from the second corner 74 to a third corner 78 of the reaction chamber 56, wherein the second solid reaction zone 66 and third solid reaction zone 68 are located. Additionally, the analytical research kit 40 can be maintained in a stationary position for a predetermined period of time, as described above.

While not shown in the Figures, the analytical research kit 10 may then be rotated counter-clockwise such that the second reaction mixture 79 is transported via gravity from the third corner 78 to the sample read window 64 in the second corner 74, provided that, in one embodiment. Any such second detectable response provided by the second reaction mixture 79 can then be measured, and the remaining assay steps, if necessary, can be carried out subsequent thereto. By way of example only and not by way of limitation, the second detectable response may be a glycated hemoglobin (HbA1c) measurement where the liquid test sample is whole blood, for example, such as when performing an assay for the percent of glycated hemoglobin (HbA1c) in a whole blood sample. In the case of a lipid-based assay, the second detectable response may be a high-density lipoprotein (HDL) cholesterol measurement where the liquid test sample is blood serum, for example, when performing an assay for the calculation of the percent of low-density lipoprotein (LDL) cholesterol present in a blood serum sample.

Figure 4:
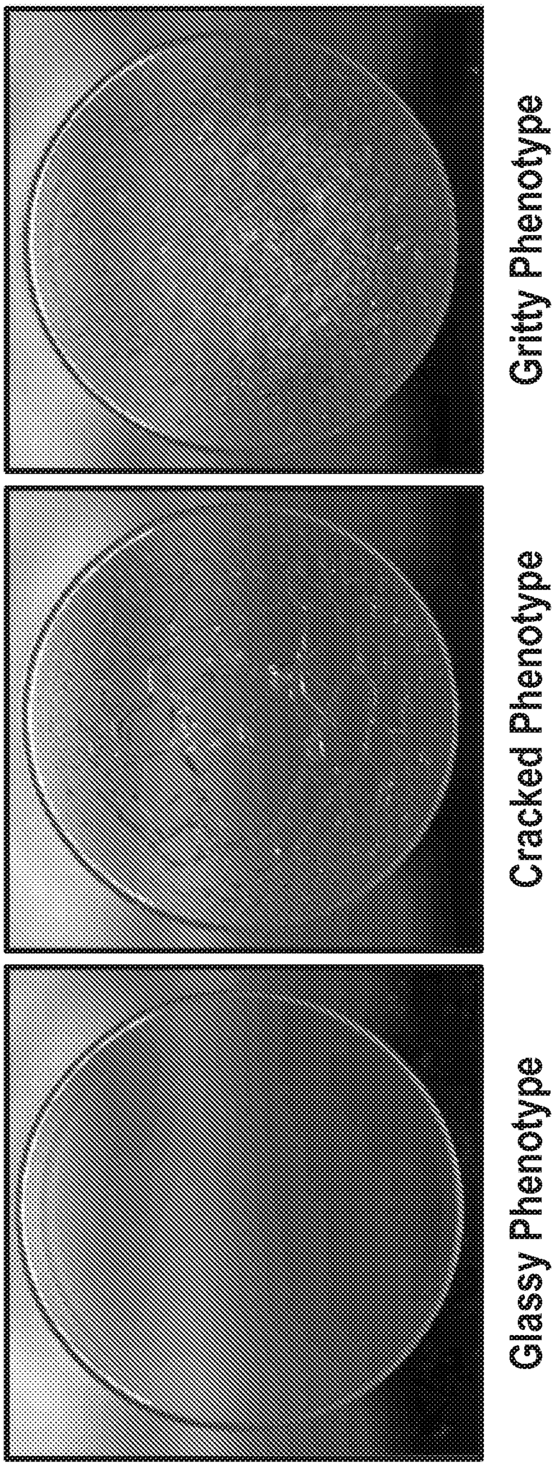
FIG. 4 are photographs showing non-limiting embodiments of a various phenotypes (including, glassy, cracked, and gritty phenotypes) of an antibody reaction zone which does not contain a concentration of at least one hydrophilic polysaccharide.

As previously mentioned, in one non-limiting embodiment the third solid reagent (for instance, by way of example, an antibody latex reagent) present on and/or in the third solid reagent zone 68 comprises and/or consists of one or more highly-concentrated sugars. Due to the high concentration of sugar, when the third solid reagent is dried (for instance, by way of example only, via conduction and/or convection drying procedure(s)) to form the mesa/node of the third solid reagent zone 68, the third solid reagent exhibits low tensile strength and has a tendency to fracture over time. As shown in FIG. 4, fracturing of the third solid reagent generally produces three distinct populations and phenotypes of the third solid reagent zone 68, including, without limitation, a glassy phenotype, a cracked phenotype, and/or a gritty phenotype.

Figure 5:
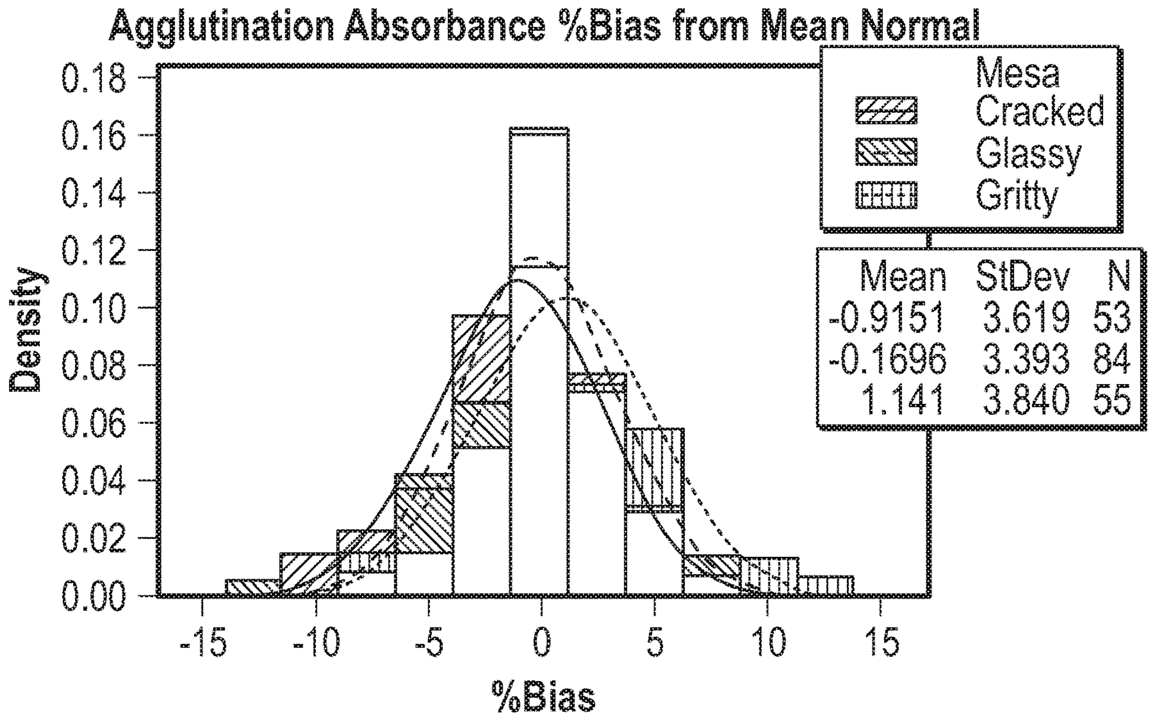
FIG. 5 is a graph plotting the relative percent bias of agglutination signal resulting from mesa/nodes comprising glassy, cracked, and gritty phenotypes.

As shown in FIG. 5, each distinct phenotype (i.e., glassy, cracked, and gritty) exhibits its own relative mean rate of agglutination that introduce varying degrees of percent bias (% bias) to the particular diagnostic assay. With respect to FIG. 5., in order to mitigate or eliminate any impact resulting from any variable other than mesa/node appearance of the third solid reaction zone 68, the % bias was taken for the delta agglutination signal against the mean for each instrument, storage condition, and test solution individually, followed by subsequent compilation of the aggregated data. Only datasets that held representative samples of all three phenotypes were used to ensure that the final set would not be artificially set to zero. As can be seen in FIG. 5, the agglutination absorbance of the glassy phenotype is closest to no bias, while the agglutination absorbance signal of the cracked phenotype is low (as compared to the mean signal) and the agglutination signal of the gritty phenotype is high (as compared to the mean signal).

Figure 6:
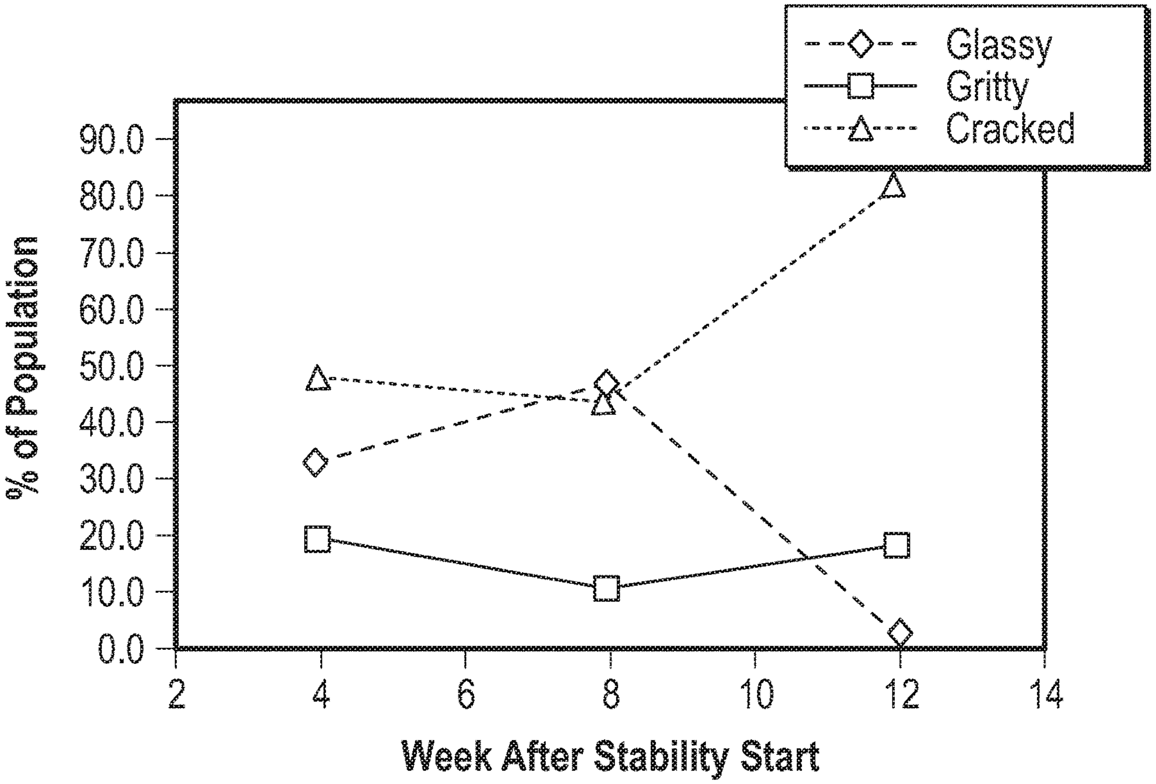
FIG. 6 is a graph plotting the qualitative appearance of a population of reaction zones constructed in accordance with the presently disclosed and/or claimed inventive concept(s) that do not contain a concentration of at least one hydrophilic polysaccharide over a period of time.

Referring now to FIG. 6, shown therein is a graphical representation of phenotypic appearance of a population of antibody latex mesas (containing no hydrophilic polysaccharide) measured over a time period of 12 weeks. As can be seen from FIG. 6, the stability/phenotype of the population of mesas trends toward the cracked phenotype, with about 80% of the population of mesas comprising the cracked phenotype at week 12.

In one non-limiting embodiment, the third solid reagent is a dried antibody latex reagent comprising gelatin and at least one sugar utilized for the detection of glycated hemoglobin present in the second reaction mixture 79. By way of example only, the at least one sugar may comprise and/or consist of monosaccharides, disaccharides, and/or sugar alcohols, including, without limitation, fructose, galactose, glucose, cellobiose, lactose, lactulose, maltose, sucrose, trehalose, mannitol, and combinations thereof.

In one non-limiting embodiment of the presently disclosed and/or claimed inventive concept(s), the third solid reagent is a dried antibody latex reagent comprised of a combination gelatin, sucrose, and trehalose and an antibody for the detection of glycated hemoglobin in the second reaction mixture 79. In this latter embodiment, when only one of the sugars is utilized, fractures (i.e., phenotypic changes in the mesa/node comprising the third solid reaction zone 68) occur at a higher frequency and at a greater severity. In addition, in this latter embodiment, it has been found that shifting away from the current ratio of trehalose to sucrose (such as, by way of example only, a ratio of trehalose to sucrose of about 7.5% and 7.5% to about 10 microliters of dispensed reagent) further increases the rate of fracturing of the mesa/node.

In one non-limiting embodiment of the presently disclosed and/or claimed inventive concept(s), the fracturing and phenotypic changes related to the mesas/nodes of the third solid reagent zone 68 comprising a dried antibody latex reagent, gelatin, and at least one monosaccharide, disaccharide, sugar alcohol, and/or combinations thereof are formulated with a predetermined concentration of at least one hydrophilic polysaccharide. The at least one hydrophilic polysaccharide acts as a surface and bond stabilizer to the gelatin and/or at least one monosaccharide, disaccharide, sugar alcohol, or combination thereof to thereby reinforce the node/mesa to mitigate or eliminate fracturing and phenotypic changes to the mesa/node. In one non-limiting embodiment, such at least one hydrophilic polysaccharide comprises, consists of, or is selected from the group consisting of cellulose, carboxymethylcellulose (CMC), FICOLL® (neutral, highly-branched, high-mass hydrophilic polysaccharide, GE Healthcare Bioscience AB, Uppsala, Sweden), starch, pullulan, maltodextrin, chitosan, chitin, dextran, arabinogalactan, and/or any combination thereof. In one non-limiting embodiment, that at least one hydrophilic polysaccharide is sodium carboxymethylcellulose.

In addition to or in lieu of at least one hydrophilic polysaccharide, at least one hydrophilic non-saccharide-based polymer may be utilized in accordance with the presently disclosed and/or claimed inventive concept(s) to stabilize the mesa/node of the third solid reagent zone 68. In one non-limiting embodiment, such at least one hydrophilic non-saccharide-based polymer comprises, consists of, or is selected from the group consisting of poly(N-isopropylacrylamide) (PNIPAM), polyacrylamide, poly(2-oxazoline), polyethylenimine, poly(acrylic acid), polymethyacrylate, acrylic-based polymers, poly(ethylene glycol), poly(ethylene oxide), poly(vinyl alcohol) (PVA), poly(vinylpyrrolidone) (PVP), polyelectrolytes, cucurbituril hydrate, collagen, lignin, and combination thereof.

As previously discussed herein, in one non-limiting embodiment, the addition of a concentration of the hydrophilic polysaccharide carboxymethylcellulose (CMC) to the dried reagent comprising gelatin and at least one monosaccharide, disaccharide, and/or sugar alcohol present in or on the mesa/node of the third solid reaction zone 68 thereby stabilizes the mesa/node and mitigates or eliminates fracturing and phenotypic changes to such mesa/node.

Figure 7A:
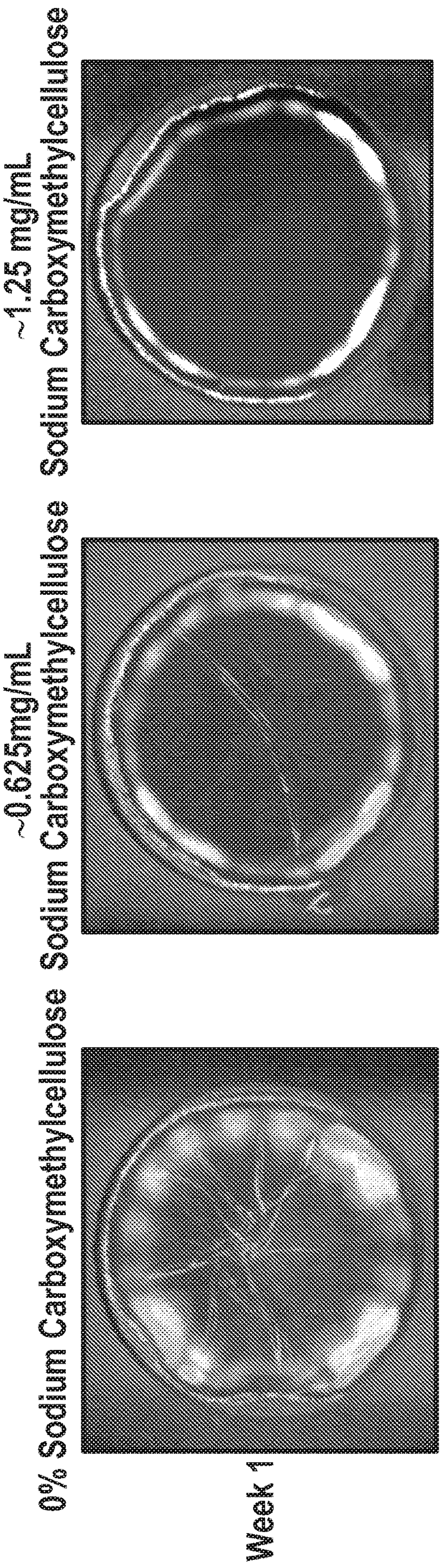
FIGS. 7A-7C are photographs showing comparative results of a non-limiting embodiment(s) of exemplary antibody reaction zone mesas comprising varying concentrations of at least one hydrophilic polysaccharide constructed in accordance with the presently disclosed and/or claimed inventive concept(s), the photographs showing the exemplary antibody reaction zone mesas after one week of storage (FIG. 7A), 2 weeks of storage (FIG. 7B), and 3 weeks of storage (FIG. 7C).
Figure 7B:
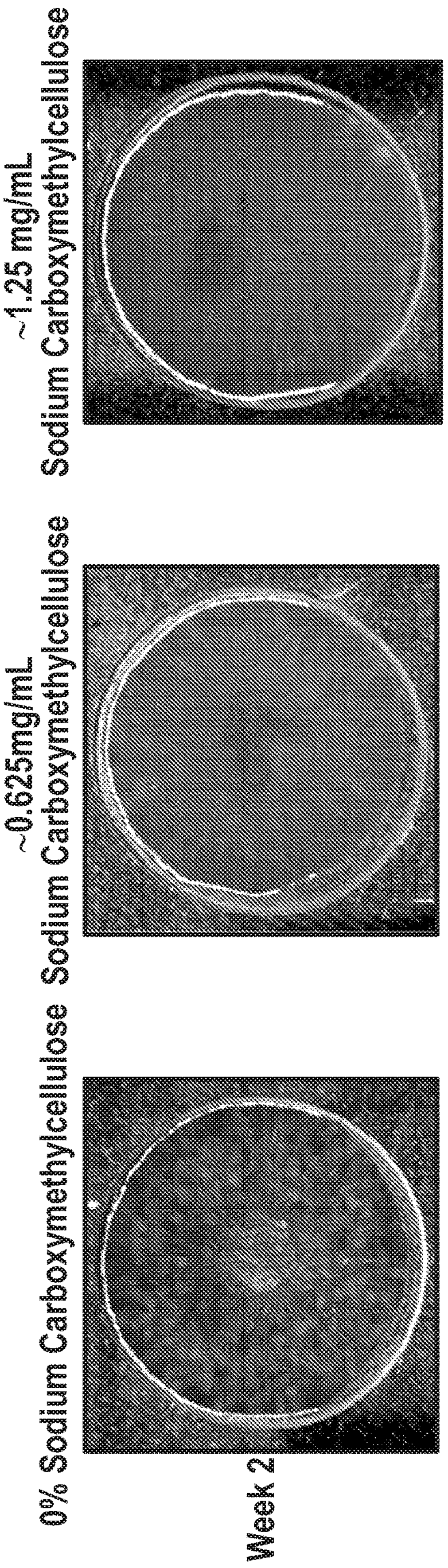
Figure 7C:
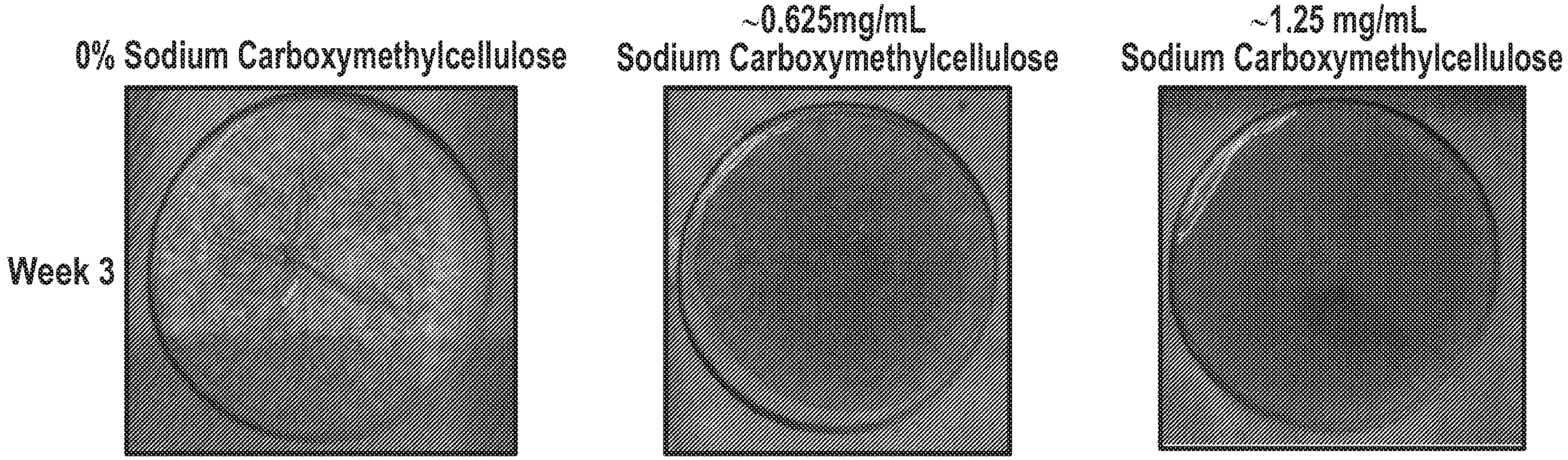

Referring now to FIGS. 7A-7C, shown therein are photographs showing comparative results of a non-limiting embodiment(s) of exemplary antibody reaction zone mesas comprising varying concentrations of at least one hydrophilic polysaccharide constructed in accordance with the presently disclosed and/or claimed inventive concept(s), the photographs showing the exemplary antibody reaction zone mesas after one week of storage (FIG. 7A), 2 weeks of storage (FIG. 7B), and 3 weeks of storage (FIG. 7C)

Referring now to FIG. 7A, shown therein are three mesas/nodes comprising three different concentrations of carboxymethylcellulose (as the hydrophilic polysaccharide) constructed in accordance with the presently disclosed and/or claimed inventive concept(s). The images in FIG. 7A were taken after one week of storage at room temperature followed by subsequent refrigeration for two days. Once a mesa/node begins to fracture, the fracturing tends to progress through a number of different phases, beginning with large fractures forming across the surface of the reagent mesa/node resulting in a cracked phenotype (as shown in the left most image of FIG. 7A). Once the cracked phenotype of the mesa/node is formed, additional fractures begin to propagate from the initial large break into many small pieces thereby forming the gritty phenotype. As can be clearly seen in the images of FIG. 7A, when a node/mesa constructed in accordance with the presently disclosed and/or claimed inventive concept(s) are formed without a concentration of at least one hydrophilic polysaccharide (such as, by way of example, carboxymethylcellulose), the mesa/node shows significant fracturing after one week of storage at room temperature. As shown in the middle and right images of FIG. 7A, as the concentration of the at least one hydrophilic polysaccharide increases (such as, by way of example only, from a range of from about 0.625 milligrams/milliliter to about 1.25 milligrams/milliliter), the fracturing is mitigated (or even eliminated) and the mesa/node resembles a glassy phenotype (with little to no fracturing) after one week of storage at room temperature. The ranges provided herein with respect to the predetermined concentration(s) of the at least one hydrophilic polysaccharide is/are not meant to be exhaustive; rather, a person having ordinary skill in the art should readily appreciate that the predetermined concentration(s) utilized in the presently disclosed and/or claimed inventive concept(s) may vary depending on, for instance, the polymer length and/or polymer branching of the at least one hydrophilic polysaccharide.

Referring now to FIG. 7B, shown therein are the three mesas/nodes from FIG. 7A, wherein the images were taken 2 weeks after storage at room temperature. As can be seen in FIG. 7B, the mesa/node that does not comprise a concentration of at least one hydrophilic polysaccharide continues to significantly increase in fracturing—especially noticeable are large fractures radiating from the center of the mesa/node. Again, as the concentration of the at least one hydrophilic polysaccharide increases, the fracturing is significantly reduced (or even eliminated) and the mesas/nodes resemble a glassy phenotype (with little to no fracturing) after two weeks of storage at room temperature.

Referring now to FIG. 7C, shown therein are the three mesas/nodes from FIG. 7A, wherein the images were taken 3 weeks after storage at room temperature. The trends observed in the images in FIGS. 7A-7B continue with mesas/nodes shown in FIG. 7C. The mesa/node that does not comprise a concentration of at least one hydrophilic polysaccharide continues to significantly increase in fracturing. Again, as the concentration of the at least one hydrophilic polysaccharide increases, the fracturing is significantly reduced (or even eliminated) and the mesas/nodes resemble a glassy phenotype (with little to no fracturing) after three weeks of storage at room temperature.

Figure 8:
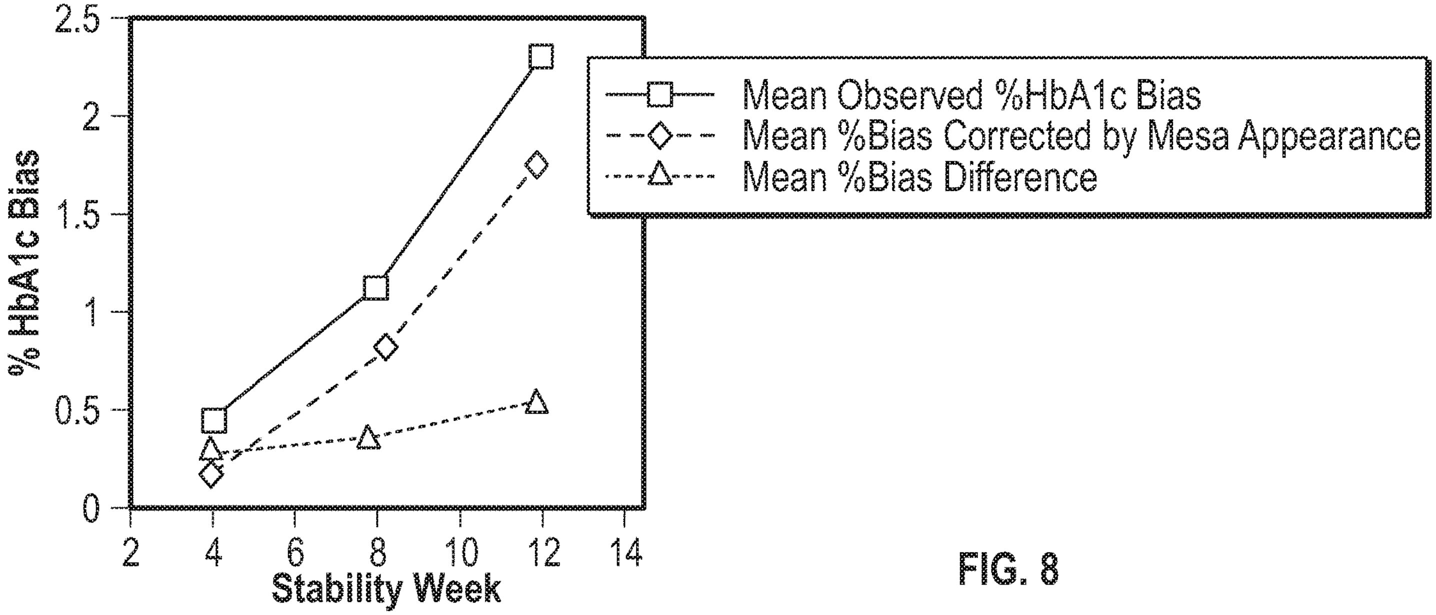
FIG. 8 is a graph plotting the percent glycated hemoglobin bias against the stability data associated with a corrected mesa state, wherein the mesa is constructed in accordance with the presently disclosed and/or claimed inventive concept(s) and does not include a concentration of at least one hydrophilic polysaccharide.

Referring now to FIG. 8, shown therein is a graph plotting the percent glycated hemoglobin bias against the stability data associated with a corrected mesa state, wherein the mesa is constructed in accordance with the presently disclosed and/or claimed inventive concept(s) and does not include a concentration of at least one hydrophilic polysaccharide. The data in FIG. 8 illustrates the mean percent glycated hemoglobin bias obtained from test solutions (represented by the square line in FIG. 8). Using the bias data correlated to mesa appearance (as shown in FIG. 5) and knowing the mesa phenotype appearance distribution for the stability dataset (as shown in FIG. 6), a bias correction can be calculated for mesa exhibiting only the glassy phenotype (represented by the diamond line in FIG. 8). As shown in FIG. 8, by the end of a 12-week room temperature shelf life, the mean bias is, utilizing mesas constructed in accordance with the presently disclosed and/or claimed inventive concept(s), reduced from over about 2.25% to about 1.75% (represented by the diamond line in FIG. 8). Accordingly, as shown in Table 1 hereinbelow, the difference between the corrected and uncorrected data set values is about 0.5% for dataset. The corrected bias results in in a reduction in the coefficient of variation (CV), thereby resulting in an increase in the repeatability and accuracy of the diagnostic assay performed. With reference to Table 1, test solution 1 (TS1) comprised about 5.36% Hb1Ac), test solution 2 (TS2) comprised about 7.8% Hb1Ac, and clinical test solution 4 (CTS4) comprised about 12.1% Hb1Ac. S Table 1: Nominal and Corrected CV Values Associated with TS1, TS2, and CTS4

TABLE 1

| Nominal and Corrected CV Values Associated with TS1, TS2, and CTS4 | | | |
|---|---|---|---|
| | Nominal CV | Corrected CV | Difference |
| TS1 | 1.84 | 1.93 | −0.09 |
| TS2 | 1.45 | 1.25 | 0.20 |
| CTS4 | 2.58 | 2.56 | 0.02 |

Figure 9A:
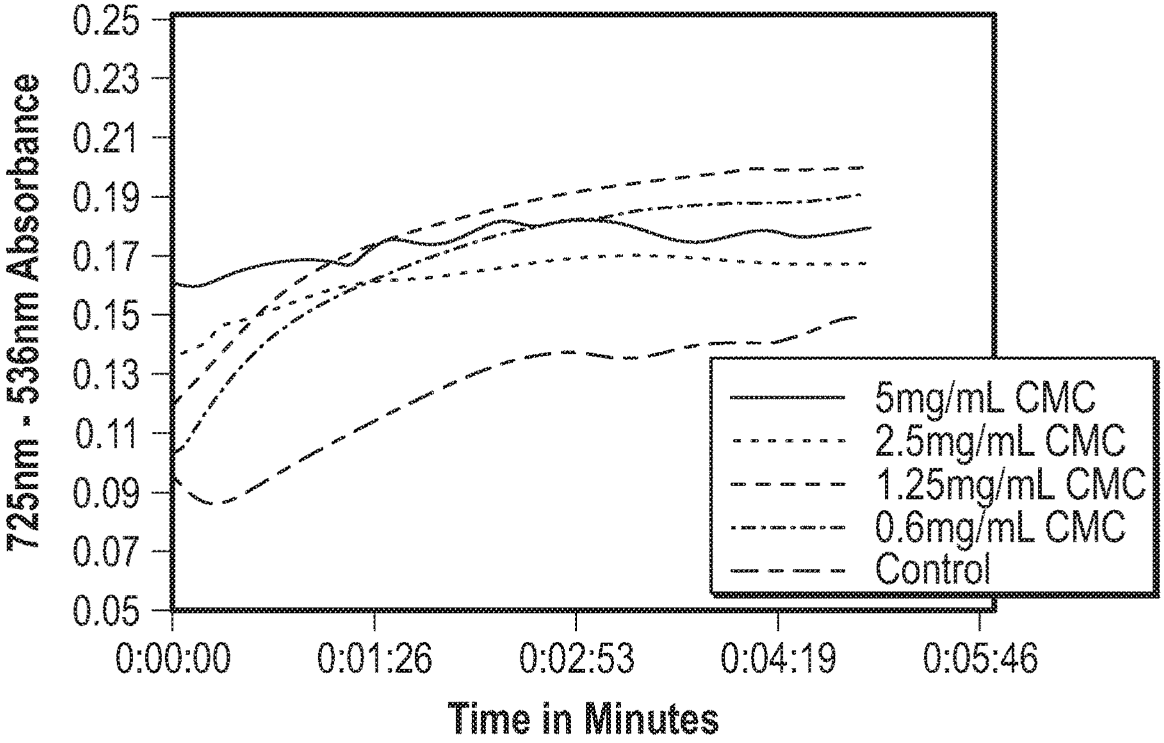
FIGS. 9A-9B are graphical representations of the assay kinetics associated with mesas constructed in accordance with the presently disclosed and/or inventive concept(s) which comprise varying concentrations of at least one hydrophilic polysaccharide, wherein the assay kinetics of the mesas are measured at wavelengths of about 725 nanometers and about 536 nanometers (FIG. 9A) and at a wavelength of about 536 nanometers (FIG. 9B).
Figure 9B:
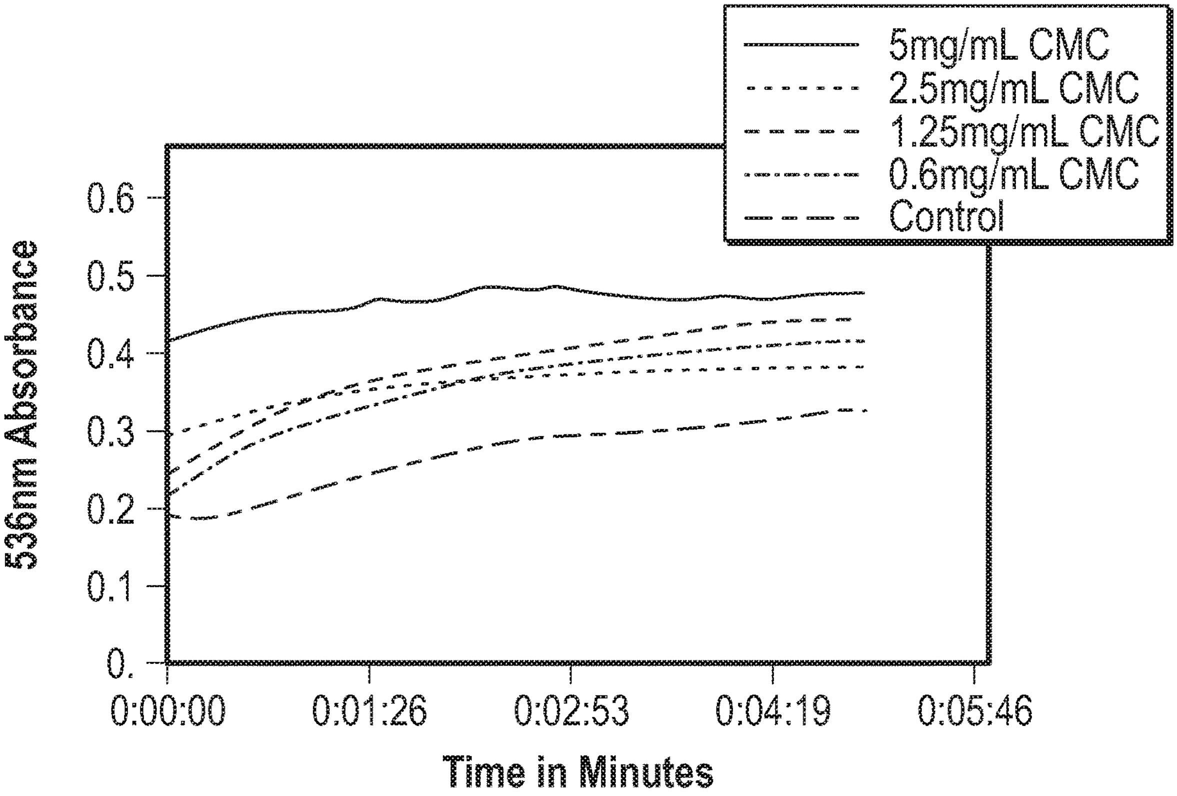

Referring now to FIGS. 9A-9B, shown therein are graphical representations of the assay kinetics associated with mesas constructed in accordance with the presently disclosed and/or inventive concept(s) which comprise varying concentrations of at least one hydrophilic polysaccharide (such as, by way of example only, carboxymethylcellulose), wherein the assay kinetics of the mesas are measured at wavelengths of about 725 nanometers and about 536 nanometers (FIG. 9A) and at a wavelength of about 536 nanometers (FIG. 9B). As can be seen in both FIGS. 9A and 9B, the higher the concentration of the at least one hydrophilic polysaccharide used, the faster the agglutination/analyte detection reaction (such as, by way of example, glycated hemoglobin detection) occurs as evidenced by increasing initial absorbance readings. Accordingly, reaction time is decreased resulting from the stability provided by the at least one hydrophilic polysaccharide that mitigates or eliminates the fracturing of the mesa/node to thereby maintain a predominantly glassy phenotype.

Non-Limiting Examples of the Inventive Concept(S)

An analytical reaction kit, the kit comprising: a reaction cassette for conducting at least one diagnostic assay, the reaction cassette comprising: a body, the body comprising a top perimeter side, a bottom perimeter side, a first perimeter side, a second perimeter side, a bottom portion, and a top portion thereby forming a reaction cassette chamber; an inlet for introducing a liquid test sample into the reaction cassette chamber; and a reaction chamber in liquid communication with the inlet, wherein the reaction chamber further comprises at least one solid reagent zone, wherein the at least one solid reagent zone comprises at least one antibody reagent zone for the detection of at least one analyte of interest present in a patient's liquid test sample, the at least antibody reagent zone comprises at least one antibody, at least one monosaccharide, disaccharide, sugar alcohol, or combinations thereof, and at least one hydrophilic polysaccharide; a liquid analytical reagent dispensing apparatus, the apparatus comprising: a container having a first end, a second end, a first side, a second side, a bottom side, a top side, a cavity being open at the top side of the container, and a flange extending around the open top of the cavity, at least one liquid reagent disposed within the cavity; and a flexible cover removably affixed to the flange of the container to seal the at least one liquid reagent in the cavity, wherein the at least one liquid reagent flows from the cavity into the reaction chamber upon removal of the flexible cover from the flange and with the first end of the container positioned substantially vertically beneath the second end of the container; and a capillary, the capillary capable of being partially inserted into the inlet of the reaction cassette to thereby introduce a liquid test sample into the reaction chamber.

An analytical reaction kit, the kit comprising: a housing for conducting at least one diagnostic assay, wherein the housing comprises a reaction chamber for the conductance of one or more diagnostic assays, the reaction chamber further comprising at least one solid reagent zone, wherein at least one of the at least one solid reagent zone comprises an antibody reagent zone for the detection of at least one analyte of interest present in a patient's liquid test sample, the antibody reaction zone comprising at least one antibody, at least one monosaccharide, disaccharide, sugar alcohol, or combinations thereof, and at least one hydrophilic polysaccharide; and a liquid analytical reagent dispensing apparatus contained within the housing, the apparatus comprising: a container, wherein the container contains at least one liquid analytical reagent, the container being in fluid communication with the reaction chamber to thereby dispense the at least one liquid analytical reagent at a predetermined time.

The analytical reaction kit, wherein the liquid test sample is a volume of whole blood.

The analytical reaction kit, wherein the volume of whole blood is in a range of from about 0.1 microliter to about 100 microliters.

The analytical reaction kit, wherein the one or more diagnostic assays are selected from a total hemoglobin detection assay, a glycated hemoglobin detection assay, and combinations thereof.

The analytical reaction kit, wherein the at least one analyte of interest is glycated hemoglobin.

The analytical reaction kit, wherein the at least one antibody comprises a glycated hemoglobin detection antibody.

The analytical reaction kit, wherein the at least one monosaccharide is selected from the group consisting of fructose, galactose, glucose, and combinations thereof.

The analytical reaction kit, wherein the at least one disaccharide is selected from the group consisting of cellobiose, lactose, lactulose, maltose, sucrose, trehalose, and combinations thereof.

The analytical reaction kit, wherein the at least one sugar alcohol comprises mannitol.

The analytical reaction kit, wherein the at least one hydrophilic polysaccharide is selected from the group consisting of cellulose, carboxymethylcellulose, FICOLL, starch, pullulan, maltodextrin, chitosan, chitin, dextran, arabinogalactan, and combinations thereof.

A method for mechanically stabilizing at least one solid reagent zone for use in at least one diagnostic assay, the method comprising the steps of: forming at least one solid reagent zone precursor, wherein the solid reagent zone precursor comprises at least one monosaccharide, disaccharide, sugar alcohol, or combinations thereof in liquid state; adding a predetermined concentration of at least one hydrophilic polysaccharide to the at least one solid reagent precursor; and drying the at least one solid reagent precursor to thereby form at least one stabilized solid reagent zone for use in the conductance of one or more diagnostic assays.

The method, wherein the at least one monosaccharide is selected from the group consisting of dextrose, fructose, galactose, glucose, and combinations thereof.

The method, wherein the at least one disaccharide is selected from the group consisting of cellobiose, lactose, lactulose, maltose, sucrose, trehalose, and combinations thereof.

The method, wherein the at least one sugar alcohol is mannitol.

The method, wherein the at least one hydrophilic polysaccharide is selected from the group consisting of cellulose, carboxymethylcellulose, FICOLL, starch, pullulan, maltodextrin, chitosan, chitin, dextran, arabinogalactan, and combinations thereof.

The method, wherein the one or more diagnostic assays is selected from a total hemoglobin detection assay, a glycated hemoglobin detection assay, and combinations thereof.

The method, wherein the stabilized solid reagent zone further comprises at least one antibody for the detection of at least one analyte of interest present in a patient's liquid test sample.

The method, wherein the at least one antibody comprises a glycated hemoglobin antibody.

The method, wherein the at least one analyte of interest is glycated hemoglobin.

The method, wherein the patient's liquid test sample is a volume of whole blood.

The method, wherein the predetermined concentration of the at least one hydrophilic polysaccharide is in a range of from about 0.5 milligrams per milliliter to equal to about 5.5 milligrams per milliliter.

Thus, in accordance with the presently disclosed and claimed inventive concept(s), there have been provided devices, kits, and methods for dispensing at least two liquid reagents for use in analyte(s) detection assays. As described herein, the presently disclosed and claimed inventive concept(s) relate to embodiments of a modified solid reaction zone for the conductance of at least one diagnostic assay, as well as kits and method related thereto. More specifically, as described herein, the presently disclosed and/or claimed inventive concept(s) relate to non-limiting embodiments of apparatus, kits, and methods for the incorporation of at least one hydrophilic polysaccharide to dried sugar reagents present in or on a solid reaction zone and/or a mesa/node thereof to thereby increase the mechanical stability of such solid reaction zone and to increase the accuracy of results obtained from the conductance of at least one diagnostic assay due to the reduction or elimination of fracturing of such solid reaction zone (for instance, an latex antibody reaction zone). Accordingly, the present disclosed and/or claimed inventive concept(s) fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. An analytical reaction kit, the kit comprising:

a housing for conducting at least one diagnostic assay, wherein the housing comprises a reaction chamber that comprises at least one solid reagent zone, wherein the at least one solid reagent zone comprises at least one antibody reagent zone for the detection of at least one analyte of interest present in a patient's liquid test sample, the at least one antibody reagent zone comprising:

at least one antibody, at least one monosaccharide, disaccharide, sugar alcohol, or combinations thereof, and carboxymethylcellulose, wherein carboxymethylcellulose is added to the at least one monosaccharide, disaccharide, sugar alcohol, or combination thereof to increase tensile strength and thereby reduce fracturing of a surface area of the solid reagent zone when compared to a solid reagent zone prepared in the absence of carboxymethylcellulose, and wherein the solid reagent zone has a stabilized surface area with substantially no fracturing and substantially no gritty surface after at least three weeks of storage at room temperature; and a liquid analytical reagent dispensing apparatus contained within the housing, the apparatus comprising:

a container, wherein the container contains at least one liquid analytical reagent, the container being in fluid communication with the reaction chamber to thereby dispense the at least one liquid analytical reagent.

2. The analytical reaction kit of claim 1, wherein the liquid test sample is a volume of whole blood in a range of from about 0.1 micro liter to about 100 microliters.

3. The analytical reaction kit of claim 2, wherein the at least one diagnostic assay is selected from a total hemoglobin detection assay, a glycated hemoglobin detection assay, and combinations thereof.

4. The analytical reaction kit of claim 2, wherein the at least one analyte of interest is glycated hemoglobin, and wherein the at least one antibody comprises a glycated hemoglobin detection antibody.

5. The analytical reaction kit of claim 1, wherein the at least one monosaccharide is selected from the group consisting of fructose, galactose, glucose, and combinations thereof.

6. The analytical reaction kit of claim 1, wherein the at least one disaccharide is selected from the group consisting of cellobiose, lactose, lactulose, maltose, sucrose, trehalose, and combinations thereof.

7. The analytical reaction kit of claim 1, wherein the at least one sugar alcohol comprises mannitol.

8. A method for increasing tensile strength at least one solid reagent zone for use in at least one diagnostic assay, wherein the at least one solid reagent zone comprises at least one antibody for the detection of at least one analyte of interest present in a patient's liquid test sample, the method comprising the steps of:

forming at least one solid reagent zone precursor, wherein the solid reagent zone precursor comprises at least one monosaccharide, disaccharide, sugar alcohol, or combinations thereof in liquid state;

adding a predetermined concentration of carboxymethylcellulose to the at least one solid reagent precursor; and drying the at least one solid reagent precursor to thereby form at least one stabilized solid reagent zone for use in the conductance of one or more diagnostic assays;

wherein at least one of:

the solid reagent zone has a stabilized surface area with substantially no fracturing and substantially no gritty surface after at least three weeks of storage at room temperature;

the solid reagent zone has a stabilized surface area that reduces a reaction time for detection of the at least one diagnostic assay when compared to a solid reagent zone prepared in the absence of carboxymethylcellulose; and/or the solid reagent zone has a stabilized surface area that reduces a percent bias of the at least one diagnostic assay when compared to a solid reagent zone prepared in the absence of carboxymethylcellulose.

9. The method of claim 8, wherein at least one of:

the at least one monosaccharide is selected from the group consisting of fructose, galactose, glucose, and combinations thereof;

the at least one disaccharide is selected from the group consisting of cellobiose, lactose, lactulose, maltose, sucrose, trehalose, and combinations thereof; and/or the at least one sugar alcohol is mannitol.

10. The method of claim 8, wherein the one or more diagnostic assays is selected from a total hemoglobin detection assay, a glycated hemoglobin detection assay, and combinations thereof.

11. The method of claim 8, wherein the predetermined concentration of carboxymethylcellulose is in a range of from about 0.5 milligrams per milliliter to equal to about 5.5 milligrams per milliliter.

12. An analytical reaction kit, the kit comprising:

a housing for conducting at least one diagnostic assay, wherein the housing comprises a reaction chamber for the conductance of one or more diagnostic assays, the reaction chamber further comprising at least one solid reagent zone, wherein the at least one solid reagent zone comprises at least one antibody reagent zone for the detection of at least one analyte of interest present in a patient's liquid test sample, the at least one antibody reagent zone comprising:

at least one antibody, at least one monosaccharide, disaccharide, sugar alcohol, or combinations thereof, and carboxymethylcellulose, wherein carboxymethylcellulose is added to the at least one monosaccharide, disaccharide, sugar alcohol, or combination thereof to increase tensile strength of a surface area of the solid reagent zone and reduce fracturing thereof when compared to a solid reagent zone prepared in the absence of; and wherein at least one of:

the increased tensile strength of the surface area of the solid reagent zone reduces a reaction time for detection of the at least one diagnostic assay when compared to a solid reagent zone prepared in the absence of carboxymethylcellulose; and/or the increased tensile strength of the surface area of the solid reagent zone reduces a percent bias of the at least one diagnostic assay when compared to a solid reagent zone prepared in the absence of carboxymethylcellulose; and a liquid analytical reagent dispensing apparatus contained within the housing, the apparatus comprising:

a container, wherein the container contains at least one liquid analytical reagent, the container being in fluid communication with the reaction chamber to thereby dispense the at least one liquid analytical reagent.

13. The analytical reaction kit of claim 12, wherein the liquid test sample is a volume of whole blood in a range of from about 0.1 micro liter to about 100 microliters.

14. The analytical reaction kit of claim 12, wherein the at least one diagnostic assay is selected from a total hemoglobin detection assay, a glycated hemoglobin detection assay, and combinations thereof.

15. The analytical reaction kit of claim 12, wherein the at least one analyte of interest is glycated hemoglobin, and wherein the at least one antibody comprises a glycated hemoglobin detection antibody.

16. The analytical reaction kit of claim 12, wherein at least one of:

the at least one monosaccharide is selected from the group consisting of fructose, galactose, glucose, and combinations thereof;

the at least one disaccharide is selected from the group consisting of cellobiose, lactose, lactulose, maltose, sucrose, trehalose, and combinations thereof; and/or the at least one sugar alcohol comprises mannitol.

* * * * *